United States Patent [19]

Hunnell et al.

[11] Patent Number: 5,188,347
[45] Date of Patent: Feb. 23, 1993

[54] COMPRESSIBLE MICROTOME OBJECT HOLDER

[75] Inventors: Jack E. Hunnell, Durham; John E. Hunnell, New Bern, both of N.C.

[73] Assignee: Triangle Biomedical Sciences, Inc., Durham, N.C.

[21] Appl. No.: 793,586

[22] Filed: Nov. 18, 1991

Related U.S. Application Data

[63] Continuation-in-part of Ser. No. 409,459, Sep. 19, 1989, Pat. No. 5,082,254.

[51] Int. Cl.⁵ .............................................. B25B 1/24
[52] U.S. Cl. ..................................... 269/258; 269/274; 269/275; 269/909
[58] Field of Search ............... 269/309, 269, 270, 253, 269/157, 160, 329, 909, 249, 258, 75, 274, 275

[56] References Cited

U.S. PATENT DOCUMENTS

| | | | |
|---|---|---|---|
| 1,697,117 | 1/1929 | Hilstad et al. | 269/75 |
| 1,936,968 | 11/1933 | Neal | 269/75 |
| 1,981,253 | 11/1934 | Schulz | 269/75 |
| 3,430,944 | 3/1969 | Pandjiris et al. | 269/258 |
| 4,034,971 | 7/1977 | Tsuyama | 269/249 |
| 4,083,624 | 4/1978 | Timmer | 269/249 |
| 4,140,307 | 2/1979 | Dalmau et al. | 269/75 |
| 4,335,873 | 6/1982 | Kiefer | 269/274 |
| 4,850,630 | 7/1989 | Davies | 269/258 |
| 5,069,433 | 12/1991 | Womack | 269/75 |
| 5,082,254 | 1/1992 | Hunnell et al. | 269/269 |

Primary Examiner—Robert C. Watson
Attorney, Agent, or Firm—Olive & Olive

[57] ABSTRACT

The present invention relates in one aspect to a compressible and/or deformable microtome object holder. The object holder may be in the same or similar shape as a wide variety of previous object holders, comprising a specimen plate having a textured or grooved surface and a shank structure. The holder may further comprise a ball element on the opposite end of the shank structure from the plate. In this instance, the ball element serves as the means of mounting the holder to the microtome. At least the grippable portion of the holder which is held by the microtome is formed of a compressible and/or deformable substance. Preferably, the holder is unitarily formed entirely of a compressible and/or deformable substance. The invention allows an object holder to be held more securely and to be molded economically.

8 Claims, 3 Drawing Sheets ns of object holders shown as examples in FIGS. 2-10, it is clear that a wide variety of structures may be used to accomplish the same purpose.

COMPRESSIBLE MICROTOME OBJECT HOLDER

This is a continuation-in-part of co-pending U.S. patent application Ser. No. 07/409,459 filed Sep. 19, 1989, now U.S. Pat. No. 5,082,254.

BACKGROUND OF THE INVENTION

1. Field of the Invention

This invention relates to object holders commonly utilized with cryostat microtomes.

2. Description of the Related Art

For histological analysis of tissue samples and determination of their physiological and pathological characteristics, microtomes are utilized to produce extremely thin sections for microscopic examination. A cryostat is a refrigerated box which includes a microtome. In some instances, it is desirable to fix the biological specimen cryogenically by cooling it to low temperatures on the order of about $-10°$ C. to about $-50°$ C. to produce a frozen "vitrified" sample for sectioning and analysis. Accordingly, cryostat microtomes have come into usage in which the microtome unit is mounted in a cooling enclosure. In such apparatus, the microtome is coupled to externally mounted controls to actuate and control the microtome. An illustrative cryostat microtome of such type is disclosed in U.S. Pat. No. 4,548,051 issued Oct. 22, 1985 to G. Moessner.

In recent years cryostat microtomes have become increasingly sophisticated, utilizing digital controls and monitoring devices affording a highly accurate, low-distortion sectioning operation. As an example, the Minotome ® Digital Microtome-Cryostat, a cryostat microtome unit commercially available from International Equipment Company (Needham Heights, Mass.), is said to permit cutting of tissue sections with a thickness of from 2 to 42 microns, in precise 2 micron increments.

For such sectioning, the microtome typically employs an object holder comprising a specimen plate as a substrate element to which the tissue sample is affixed by an adhesive embedding medium. The specimen plate bearing such tissue sample then is clamped or otherwise fixedly positioned in the microtome apparatus, in proximity to a knife or blade which is translatable into cutting contact with the mounted specimen, to yield thin cut sections of tissue or other specimens for analysis.

With such precision sectioning ability, it is critically important in the operation of the microtome that the mounted specimen be retained in a spatially fixed position, since any movement of the specimen relative to the precision controlled cutting blade will produce sections of uneven thickness. Such variability in turn introduces a distortion and possible error into the subsequent microscopic analysis of the tissue, and may lead to mis-characterization or mis-diagnosis of the tissue, or else require discarding of the sample and repetition of the sectioning effort.

The requirement that the specimen plate be fixedly positioned and positionally constant during the sectioning operation, and the capability of the specimen holder to be relatively repositioned for subsequent sectioning operations, are frequently at odds with one another in the specimen plate assemblies which have been devised to date. There have been a number of object holders and microtome assemblies that have been devised to address this problem. As one can see from the different configu- Examples of object holders include the Minot ® object holder of the International Equipment Company (Needham Heights, Mass.), used in the International Minot Custom Microtome. The object holder features a specimen plate and stem and is fastened to the microtome generally by a screw pressure on the side of the stem which is inserted into a clamp device featuring an opening communicating with a generally spherical interior cavity. Other object holders are discussed in the description of the invention herein.

The co-pending parent U.S. patent application Ser. No. 07/409,459, provides a specimen holder mounting structure which accommodates selective fixed positioning of a ball-mounted specimen plate in a manner which is highly resistant to movement during operation of the microtome, and which at the same time is readily selectively repositionable to different orientations. The specimen holder mounting structure utilizes only a single adjustment element. The ball-mounted specimen plate is readily adjustable, both rotationally and translationally, to a subsequently desired fixed position. The disclosure of this copending application is incorporated herein by reference.

The above microtome specimen (object) holders are traditionally fabricated out of various metals such as brass or stainless steel. Due to the smoothness of fabrication of these metallic holders and their hardness, any of the previous holders even if held by contact with two or more points of the microtome's holding mechanism may be susceptible to slippage or rotation during the cutting operation or due to vibrations or movements of the microtome.

It is therefore an object of this invention to provide a microtome object holder which is compressible, and temporarily deformable so that it can be held more firmly in the microtome.

Because of the material and sometimes the cost of construction, prior object holders are also often considered permanent and are not disposable. The non-disposable nature of the holders may require that the user take the time to sterilize the holder if specimens present risks to the user or could possibly contaminate subsequent specimens on the holder or the technician. Thus, if the specimen possibly contains a hazardous agent, such as HIV or hepatitis virus, the person using the microtome may wish to dispose of the contaminated object holder and use a new uncontaminated object holder.

It is therefore a further object of this invention to provide a microtome object holder which is disposable.

Other objects and advantages will be more fully apparent from the following disclosure and appended claims.

SUMMARY OF THE INVENTION

The present invention relates in one aspect to a compressible and/or deformable microtome object holder. The object holder may be in the same or similar shape as a wide variety of previous object holders. Thus, the object holder comprises a specimen plate having a textured surface and may further comprise a shank structure, or a shank structure and a ball element, for attaching the holder to a microtome.

In any case, in the instant invention, at least the portion of the object holder which is held by the microtome is formed of a compressible and/or deformable substance and is attached by means known in the art to the remainder of the object holder which is preferably also made of a compressible and/or deformable substance. Preferably, the holder is unitarily formed entirely of a compressible and/or deformable substance.

Other aspects and features of the invention will be more fully apparent from the following disclosure and appended claims.

Figure 1:
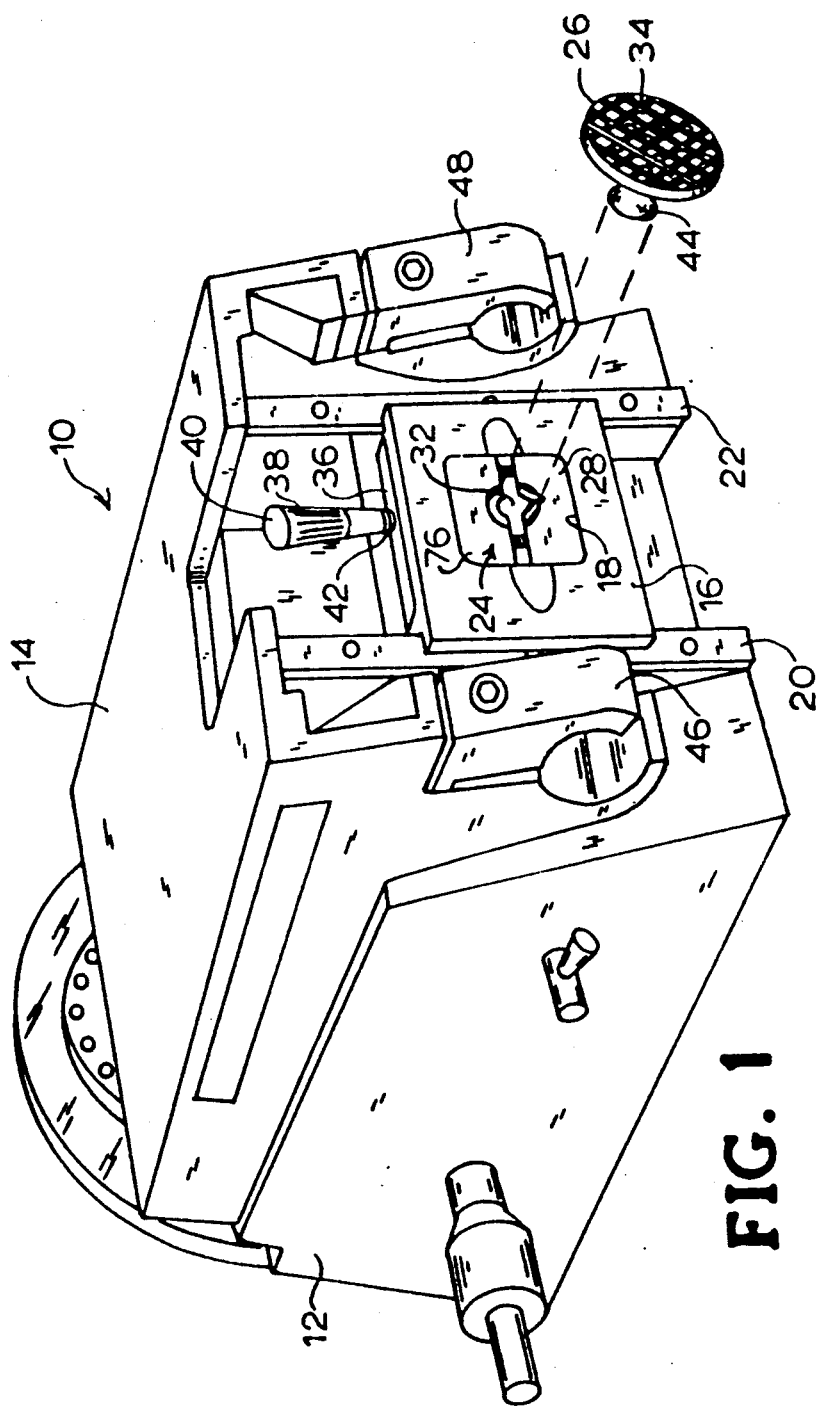
FIG. 1 is a perspective view of a microtome which may be used with the present invention.

DETAILED DESCRIPTION OF THE INVENTION AND PREFERRED EMBODIMENTS THEREOF,

The object holder of the invention has various configurations that are suitable for use with various types of microtomes, each of which object holders has at least one portion which is compressible and/or deformable, depending on the mechanism by which the microtome holds object holders. Thus, the invention in particular is an object holder for use in a microtome that has a clamping means for a portion of said object holder, said object holder comprising:

(a) a specimen plate having a grooved planar surface and a second surface generally parallel to the plane of the grooved surface;

(b) at least one grippable portion extending from the specimen plate, said grippable portion being compressible when clamped by the microtome.

The words "compressible" or "deformable" or "deformed" when used to describe the invention herein mean that when a localized pressure is applied to the compressible or deformable object, the surface of the object is pressed inward (for example by compression of the substance and/or by deformation of the shape of the object) where the pressure is applied. When used alone the word "compressible" includes object holders capable of deformation and other structural changes in the object holder due to the object holder being clamped in the microtome. The extent and permanence of alteration of the structure of the object holder depend on the material of which the object holder is made and the type of pressure applied. Thus, for a solid rubber object holder, the surface may be held slightly inward (compressed or deformed) only while the pressure is maintained, and the object holder will have little or no memory of the pressure when it is removed. A severe or very pointed, acute pressure may, however, break the surface. With more malleable materials, the pressure may result in some lasting deformation of the surface after the pressure is removed. Such materials may be usable many times but may have a more limited life due to residual deformation.

The ideal substance used in making the object holder of the invention can withstand cryogenic temperatures as used for sample storage and sectioning on the object holder, has minimal lasting deformation when clamped by a microtome, and is sufficiently compressible/deformable under pressures generally applied in the particular microtome and using the particular clamping mechanism found in the microtome to provide a grip that is more firm, due to the compression/deformation, than with the prior object holders of metal or other hard substances.

Thus, the preferred substances comprise materials, such as fiber-reinforced epoxy or polyimide materials or fiber-reinforced polypropylene materials which are compressible, compressible or deformable plastics; olefins such as polyethylene and polypropylene formulations with compressibility; synthetic elastomers such as neoprene; rubbers; and acrylonitrile butadiene styrene.

In each embodiment of the invention, the compressible/deformable portion may suitably be formed integrally with the remainder of the object holder, for example, by casting or molding, or alternatively may be separately formed and then treated to yield a surface for attachment of the remainder of the object holder.

The invention utilizes compressible and/or deformable material, so that contact of the microtome clamping members with the object holder functions to compress, deform or crush the object holder to facilitate retention of the object holder in the clamping assembly. Such construction may be employed to form a disposable object holder which is formed of low cost thermoplastic or other suitable material of construction.

Further, it is within the purview of the present invention to provide a disposable object holder which may only be partially compressible, deformable or crushable in contact with clamping members. It is also within the purview of the present invention to provide one or more of the contacting surfaces of the object holder with textured, abraded, toothed, or other surface structure serving to enhance the grippability of the object holder by the clamping members.

The words "shank", "foot", and "stem" as used herein refer to one or more portions of an object holder which may extend, for example, perpendicularly away from and below the surface of the specimen plate on which the specimen is placed, or laterally from at or below the surface of the specimen plate. When used in the specification and claims of the invention herein, the term "shank structure" refers to any such shank, foot or stem structure. A shank, foot or stem structure when present is preferably structured as shown in FIGS. 2–10 herein. A ball portion may be attached or attachable to certain embodiments of the shank portion.

A "grippable portion" as used herein refers to a shank structure and/or a ball portion of an object holder which is held tightly by a microtome, with pressure being placed on the object holder by the clamping mechanism of the microtome at the grippable portion. Generally the grippable portion is a shank structure extending perpendicularly or laterally away from a planar specimen plate and/or is a ball portion attached either to a shank structure, or potentially, directly to the specimen plate.

Figure 2:
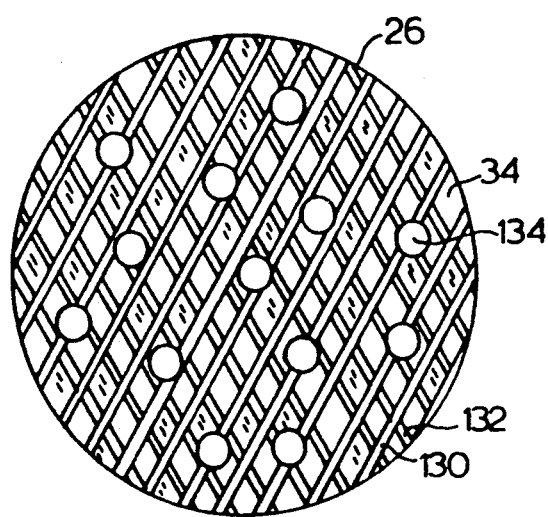
FIG. 2 is a front elevation view of a ball-mounted diagonally grooved specimen plate which is useful as part of the object holder of the present invention.
Figure 5:
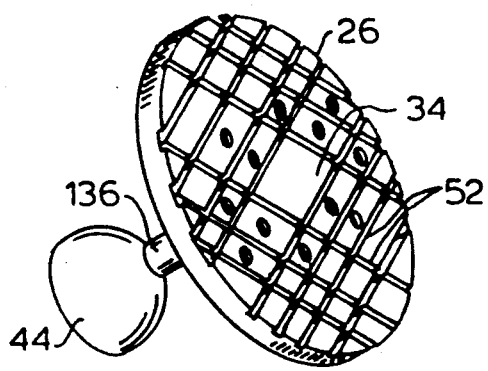
FIG. 5 is a perspective view of the object holder of FIGS. 2-4 having perpendicular grooves on the plate.
Figure 6:
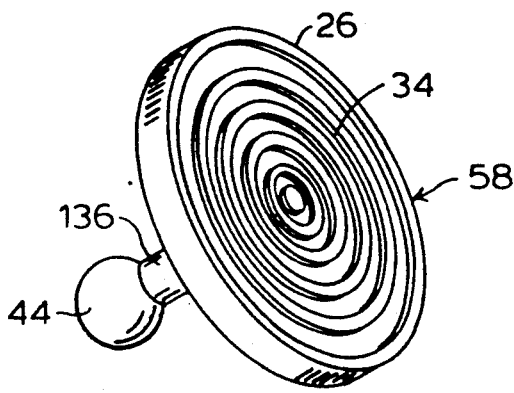
FIG. 6 is a perspective view of a second object holder which may be made according to the invention.
Figure 8:
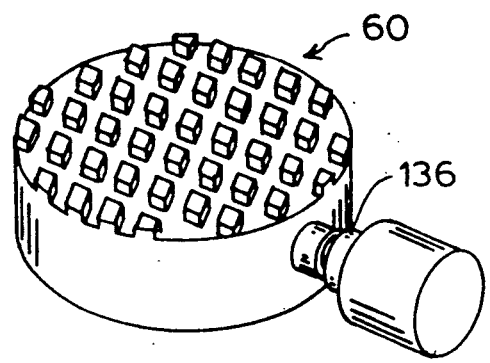
FIG. 8 is a perspective view of a fourth object holder which may be made according to the invention.
Figure 10:
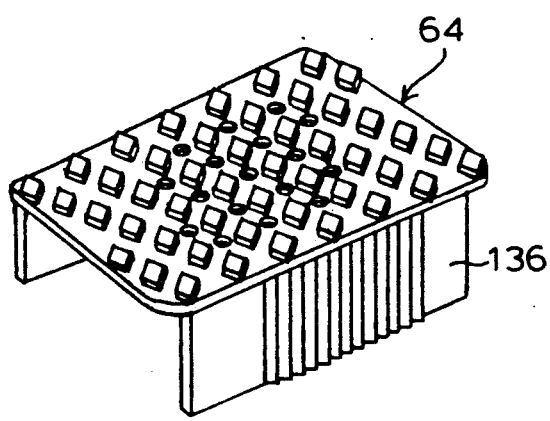
FIG. 10 is a perspective view of an object holder with a square specimen plate which may be made according to the invention.

As used herein the word "grooved" when applied to the specimen-holding surface of the object holder means a surface having straight linear, circular or other depressions in the surface or having sufficient intersecting depressed areas to form protrusions from an otherwise depressed surface as shown, for example, in FIGS. 6, 8 and 10. In addition, the specimen-bearing surface may have holes extending partially or entirely through the specimen plate as shown in FIGS. 2 and 5.

Referring now to the drawings in more detail, FIG. 1 shows a perspective view of an example of a microtome which may be used with the embodiments of FIGS. 2-5 of the present invention as discussed in the previous application. Other microtomes as known in the art may be used with the remaining embodiments of the invention.

The microtome 10 illustratively shown in this drawing is of a type as more fully described in U.S. Pat. No. 3,212,379 issued Oct. 19, 1965 to J. B. McCormick, et al., the disclosure of which hereby is incorporated herein by reference. Such a microtome is commercially available as Microtome Model 4551 from the Ames Division of Miles Laboratory, Inc. (Elkhart, Ind.) and may suitably be mounted in a cryostat for sectioning of frozen specimens.

The microtome 10 comprises a walled housing 12 having a top wall 14 which is slidably moveable in a generally horizontal plane. On the front portion of the housing is provided an upstanding wall 16 with an elongated generally vertically disposed opening 18 and a pair of vertically disposed, horizontally spaced guides 20, 22 positioned adjacent the opening. An object holder clamping assembly 24 is positioned within the opening 18, which is constructed and arranged to retentively engage ball-mounted specimen plate 26 as described in the co-pending application.

The object holder clamping assembly comprises a first clamping member 28, and a second clamping member 76, which are selectively positionable in clamping relationship relative to one another. A central cavity 32 is defined by corresponding channels in each clamping member. In the microtome 10 as illustrated, wall 16 is positioned for reciprocal sliding movement on the guides 20 and 22, so as to move the specimen bearing surface 34 of the specimen plate 26 in a plane generally perpendicular relative to a knife or disposable blade.

Mounted on the upper end of the upstanding wall 16 is a generally horizontal end plate 36, on which is mounted an adjustment screw member 38 with a manually grippable handle portion 40 which can be tightened or loosened to bring first and second clamping members 28 and 76 closer together when screw member 38 is tightened. Movement of screw member 38 and first and second clamping members allows locking and unlocking of ball 44 in cavity 32.

The microtome 10 also includes a mechanism (not shown) for holding a knife (not shown) or a disposable blade holder (not shown) which are held in position by clamping arms 46 and 48, so that the knife is in adjacent relation to the specimen-bearing surface 34 of the object holder. Such knife includes a cutting edge disposed at a slight angle to the specimen mounting surface 34. Means are provided with various models of microtome to effect the movement of either the object holder or the disposable blade holder/knife to cut slices sequentially from a sample by movement of the object holder and the affixed specimen and/or by movement of the knife.

As indicated, the structure and function of the microtome 10, with the exception of the object holder clamping assembly 24 and ball-mounted specimen plate 26, is set out in greater detail in the aforementioned U.S. Pat. No. 3,212,379. Other microtomes known in the art may be used with object holders of differing structures as discussed below.

A wide variety of object holder structures are known in the art employing various mechanisms to allow clamping or other types of holding by the microtome. Thus, the invention contemplates a series of new object holders, having varying structures, such as stem only, ball and stem, double flattened stems or solid block similar in appearance to those known in the art, etc., but which are compressible in at least the portion of object holder which is clamped or otherwise held on the microtome.

Figure 3:
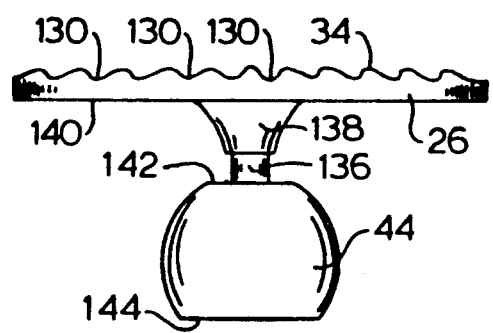
FIG. 3 is a side elevation view of ball-mounted object holder of FIG. 2 comprising a specimen plate, a stem and a ball.
Figure 4:
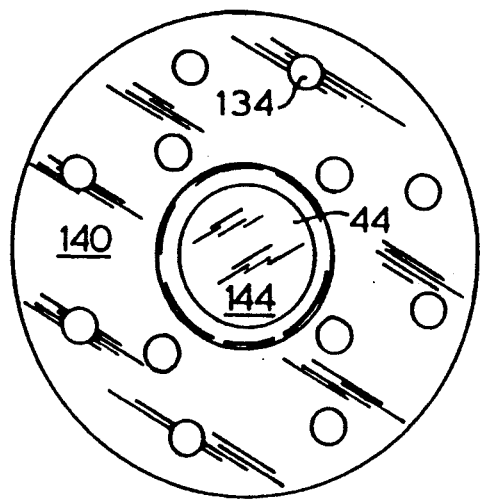
FIG. 4 is, a rear elevation view of the ball-mounted specimen plate of FIGS. 2 and 3.

FIG. 2 shows the front face of a ball-mounted specimen plate 26 according to the embodiment of the object holder shown in the co-pending application, which is shown in side elevation view in FIG. 3, and with the reverse side being illustrated in FIG. 4.

The ball-mounted specimen plate 26 of this first embodiment comprises a front specimen-bearing surface 34 on which is provided grooves. The grooves may be configured in a number of ways, for example a series of diagonally or perpendicularly intersecting grooves 130 and 132, and 52 (FIGS. 4 and 5 respectively) or a spiral (FIG. 6), etc. The grooves or concentric rings, particularly if intersecting, facilitate mounting of a selected specimen on the front specimen-bearing surface 34 of the specimen plate 26 by means of a suitable adhesive medium for embedding the specimen. To further enhance adhesion, the specimen plate 26 may feature an array of holes 134 extending therethrough, into which the embedding medium may spread and thereby "anchor" the embedded specimen. Such anchoring is important so that the embedded specimen does not break away from the specimen plate when the knife cuts across the mounted specimen.

As shown in the side elevational view of FIG. 3, the rear surface 140 of the specimen plate 26 has centrally joined thereto an attachment hub 138. The hub in turn is joined to the stem 136 of the ball 44. In the broad practice of the invention, it may be suitable to employ a ball of substantially full spherical shape for mounting in the cavity defined by the proximately positioned first and second clamping members, depending on the structural characteristics of the microtome in which the specimen holder clamping assembly of the present invention is employed.

Preferably, the rear face 144 of the ball, as shown in FIG. 3, has been ground flat, so that the face is generally parallel to the plane of the specimen plate 26. The provision of flat face 144 may be advantageous to enable proper clearance of the ball in the microtome when the ball is positioned in the cavity 32 defined by the clamping members (see FIG. 1). The provision of the flat face 144 on the ball has the further advantage that it enables the ball-mounted specimen plate to be stacked on a flat surface, such as a shelf in the cooling enclosure of a cryostat microtome.

FIG. 4 is a rear elevation view of the ball-mounted specimen holder of the first embodiment, showing the central arrangement of the ball 44 relative to the rear surface 140 of the specimen plate.

Holders with a round or spherical ball 44 which may be made to be compressible according to the invention also include the accessory universal holder and orientable object holders of the Bright Instrument Company Limited sold by Hacker Instruments Inc., Fairfield, N.J. The orientable object holder 58 is shown in FIG. 6. As with the embodiment shown in FIGS. 2-4, this type of object holder is generally held by pressure on the ball 44 at the end of the stem 136.

Figure 7:
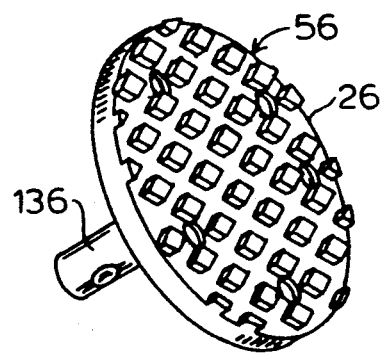
FIG. 7 is a perspective view of a third object holder which may be made according to the invention.

In a third embodiment, another object holder which may be made according to the invention herein is the Minot ® specimen holder 56 which is held in place by pressure against the side of the stem (FIG. 7). In this case, the invention provides at least a compressible stem.

Figure 9:
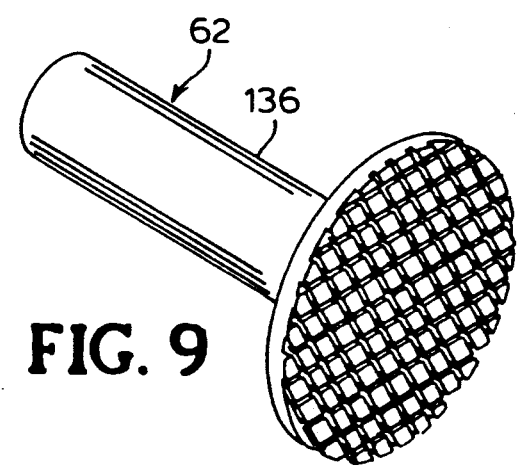
FIG. 9 is a perspective view of a straight-shank object holder which may be made according to the invention.

The Leitz microtome (Leitz 1512K) uses a fourth embodiment of an object holder 60 shown in FIG. 8 has a grippable stem piece 136 extending laterally from below the specimen-bearing surface 34. Object holders without a ball also include the straight-shank microtome object disk 62 (Lipshaw Model 800B, Lipshaw Corp., Detroit, Mich.) (FIG. 9). In this case, when made according to the invention, the object holder has at least a compressible shank 136.

A square specimen plate 64 is found in the Miles Tissue-Tek ® solid and perforated object holders (Miles, Inc.) (FIG. 10). In this case the object holder is held by pressure on the side of the holder including the dual side pieces (termed shanks 136 herein). In the invention, the dual side pieces may be replaced by a solid block to increase structural strength of the compressible shank area.

In summary, in each embodiment of the object holder discussed above and shown in FIGS. 2-10, either a shank structure or ball of the object holder is clamped in the microtome for use in sectioning a specimen attached to the specimen plate. The invention requires that at least the portion of the object holder which is clamped be compressible and/or deformable when clamped in the microtome. Preferably the entire object holder is made in one piece of the compressible/deformable material.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An object holder for use in a microtome having a clamping means for clamping a portion of an object holder, said object holder comprising:
   (a) a specimen plate having a grooved planar surface and a second surface generally parallel to the plane of the grooved surface; and
   (b) at least one grippable portion extending from the specimen plate, said grippable portion being compressible when clamped by the microtome.

2. An object holder for use in a microtome according to claim 1, wherein the grippable portion is an elongated shank structure extending from the second surface.

3. An object holder for use in a microtome according to claim 2, wherein the object holder is formed in one-piece of a compressible material.

4. An object holder for use in a microtome according to claim 1, wherein the grippable portion comprises a ball-portion attached to the specimen plate by an elongated shank structure, said ball-portion being distal from said specimen plate.

5. An object holder for use in a microtome according to claim 4, wherein the object holder is formed in one-piece of a compressible material.

6. An object holder for use in a microtome according to claim 5, wherein the ball-portion has a flat surface distal from said shank structure and generally parallel to said planar surface.

7. An object holder according to claim 1, wherein the grooved planar surface has diagonal intersecting grooves.

8. An object holder according to claim 1, wherein the grooved planar surface has perpendicular intersecting grooves.

* * * * *